US006280893B1

(12) United States Patent
Takano et al.

(10) Patent No.: US 6,280,893 B1
(45) Date of Patent: *Aug. 28, 2001

(54) ELECTROPHOTOGRAPHIC PHOTORECEPTOR

(75) Inventors: Mitsuyo Takano; Hiroki Suzuki, both of Kofu (JP)

(73) Assignees: Shindengen Electric Manufacturing Co., Ltd., Tokyo; Yamanashi Electronics Co., Ltd., Yamanashi, both of (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,280

(22) PCT Filed: Jul. 3, 1998

(86) PCT No.: PCT/JP98/03004

§ 371 Date: Mar. 3, 1999

§ 102(e) Date: Mar. 3, 1999

(87) PCT Pub. No.: WO99/01798

PCT Pub. Date: Jan. 14, 1999

(30) Foreign Application Priority Data

Jul. 4, 1997 (JP) .................................................. 9-195053

(51) Int. Cl.[7] ............................ G03G 5/047; C07C 50/06

(52) U.S. Cl. ............................ 430/58.25; 430/56; 430/70; 430/83; 552/293; 552/304

(58) Field of Search .................................... 430/58.25, 56, 430/70, 83, 59.2, 78, 59.5; 552/304, 293; 558/389

(56) References Cited

U.S. PATENT DOCUMENTS

| | | | |
|---|---|---|---|
| 5,565,288 | 10/1996 | Watanabe et al. | 430/70 |
| 5,942,359 * | 8/1999 | Kinoshita et al. | 430/58.25 |

FOREIGN PATENT DOCUMENTS

| | | |
|---|---|---|
| 5-142813 | 6/1993 | (JP) . |
| 8-15878 | 1/1996 | (JP) . |
| 8-278647 | 10/1996 | (JP) . |
| 8-305052 | 11/1996 | (JP) . |
| 9-34141 | 2/1997 | (JP) . |
| 9-101622 | 4/1997 | (JP) . |

OTHER PUBLICATIONS

Patent & Trademark Office English–Language Translation of Japanese Patent 8–305052, Which was Published Nov. 22, 1996.*

Japanese Patent Office Abstract of Japanese Patent 08–305052 (Pub 11/96).*

Derwent Abstract Acc.No. 1997–056713 of Japanese Patent 08–305052 (Pub 11/96).*

A. McKillop et al., "A Simple and Efficient Procedure for the Preparation of p–Quinols by Hypervalent Iodine Oxidation of Phenols and Phenol Tripropylsilyl Ethers", J. Chem. Soc. Perkin Trans., p. 2047–2048, (1994).

M. Bryce et al., "New Electron Acceptors: Synthesis, Electrochemistry, and Radical Anions of N,7,7–Tricyanoquinomethanimines and X–ray Crystal Structures of the Trimethyl and Tetramethyl Derivatives", J. Org. Chem, 57 (6) :1690–1696, (1992).

A. Nishinaga et al., "Baseninduzierte Acyloin–Umlagerung sterisch gehinderter p–Chinole", Chem. Ber., 109:1530–1548, (1976), paritial translation.

* cited by examiner

*Primary Examiner*—Janis L. Dote
(74) *Attorney, Agent, or Firm*—Finnegan, Henderson, Farabow, Garrett & Dunner, LLP

(57) ABSTRACT

Electrophotographic photoreceptors for use in photocopiers and laser printers, among other things, possessing high electron mobility and superior photosensitivity properties. The photoreceptors of the invention utilize a photosensitive layer with a carrier transport material containing a compound which exhibits high molecular vibration. The compounds of the invention are electron transfer agents which can be dispersed in a photosensitive layer at a high concentration and can be molecularly designed to have a desired magnitude of molecular vibration.

3 Claims, 10 Drawing Sheets

ELECTROPHOTOGRAPHIC PHOTORECEPTOR

FIELD OF THE INVENTION

The present invention relates to electrophotographic photoreceptors for use in, for example, photocopiers or laser printers, and particularly to electrophotographic photoreceptors using organic thin films and electron transfer agents used therefor.

PRIOR ART

Inorganic thin films made of inorganic materials such as selenium, selenium-tellurium, selenium-arsenic, amorphous silicon were originally used as photosensitive layers in electrophotographic photoreceptors of electrophotographic apparatus such as photocopiers or laser printers.

However, electrophotographic photoreceptors having photosensitive layers using organic thin films in place of conventional inorganic thin films have been prevailing to meet recent demands for inexpensive and less pollutive electrophotographic photoreceptors. Such photosensitive layers consisting of organic thin films are mainly classified by structure into monolayer-dispersed type and function-separated type.

Monolayer-dispersed type of photosensitive layers consist of a monolayer film comprising a carrier generation material in a medium for a carrier transport material, whereby the monolayer film has both functions of generating and transporting charge carriers. On the other hand, function-dispersed type of photosensitive layers consist of a multi-layer film in which are layered a carrier generation layer (CGL) having a function of generating charge carriers and a carrier transport layer (CTL) having a function of transporting generated charge carriers.

At present, both types of photosensitive layers are commercialized, but there is a demand for developing a carrier transport material with high mobility to improve sensitivity for both types.

Organic photosensitive layers are also classified by charge type into positively charged photosensitive layers and negatively charged photosensitive layers. Most of presently known and commercialized carrier transport materials with high mobility are hole transfer type, so that commercially available electrophotographic apparatus use photoreceptors having negatively charged photosensitive layers.

However, corona discharge phenomenon used for negatively charging photosensitive layers produces a large amount of ozone as discharge occurs to pollute interior environments, accelerate deterioration of electrophotographic photoreceptors or otherwise cause various disadvantages.

Some attempts were made to eliminate disadvantages encountered during negatively charging photosensitive layers of electrophotographic apparatus of the prior art by, for example, adding an ozone-trapping filter or adopting a special ozone-free charging system, but additional problems occur such as increased bulk of apparatus or complication of electrophotographic processes and no solution has been attained.

In order to ameliorate such circumstances, recent markets require positively charged photoreceptors less likely to generate ozone, thus needing a development of an electron transfer agent with high mobility suitable for positively charged photosensitive layers.

Such electron transfer agents so far found to be suitable for positively charged photoreceptors by previous eager studies include trinitrofluorenone (TNF), tetracyanoethylene, tetracyanoquinodimethane (TCNQ), quinone, diphenoquinone, naphthoquinone, anthraquinone and derivatives thereof, etc. However, most of these electron transfer agents are less compatible with binder resins so that they can not be homogeneously dispersed in photosensitive layers at a high concentration. Thus, the content is not sufficient to satisfy electric characteristics. Asymmetric diphenoquinone compounds exceptionally show good compatibility with resins and high electron mobility, but they are so strongly colored that such compounds in photosensitive layers absorb rays which should reach carrier generation materials to lower the sensitivity.

Our examination of compounds described in JPA No. 34141/97 as electron transfer agents which solved the above problems revealed that, among compounds of the following general formula (1):

(1)

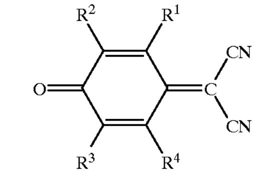

a compound wherein $R^2$ and $R^3$ represent a tBu group as represented by the following formula (5):

(5)

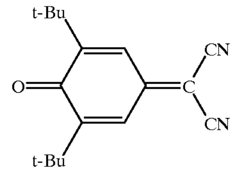

is more likely to increase sensitivity while a compound wherein $R^2$ and $R^3$ represent an Me group as represented by the following formula (6):

(6)

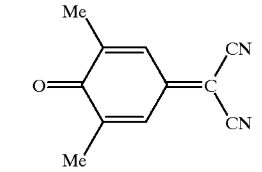

is difficult to increase sensitivity.

Assuming that the above difference in photosensitive characteristics between structures of compounds results from the difference in the stereostructure of molecules of compounds, we determined the stereostructure of molecules by the molecular orbital method.

The results are shown in FIGS. 1 and 2. FIGS. 1_a_, 1_b_, 1_c_ show the stereostructure of the molecule of the compound represented by the above chemical formula (5), while FIGS. 2_a_, 2_b_, 2_c_ show the stereostructure of the molecule of the compound represented by the above chemical formula (6). In FIGS. 1_a_, 1_b_, 1_c_ and FIGS. 2_a_, 2_b_, 2_c_, FIGS. 1_a_ and 2_a_ show the neutral state, FIGS. 1_b_ and 2_b_ show the state wherein one electron has been given, and FIGS. 1_c_ and 2_c_ show the state wherein two electrons have been given. Each of FIGS. 1*a*, 1*b*, 1*c* and FIGS. 2*a*, 2*b*, 2*c* shows a plan view on the upper side and a side view on the lower side. In these figures, hydrogen atoms are omitted, and carbon atoms and nitrogen atoms are represented by open circles while oxygen atoms are represented by solid circles (similarly to FIGS. 3*a*, 3*b*, 3*c*, FIGS. 4*a*, 4*b*, 4*c* and FIGS. 5*a*, 5*b*, 5*c* described later).

As shown in FIG. 1*a*, the ring of the compound of the above chemical formula (5) is strained in the neutral state because of the presence of a bulky substituent such as tBu group.

When electrons are given in this state, it was found that the strain decreases and a slight torsion occurs in the dicyanomethylene group as electrons increase, as shown in FIGS. 1*b*, 1*c*.

However, the ring of the compound of chemical formula (6) is not strained in the neutral state as shown in FIG. 2*a*, and no change occurred in the ring with no torsion in the dicyanomethylene group even if one or two electrons were given, as shown in FIGS. 2*b*, 2*c*.

Thus, a molecular structure deformed by giving electrons seems to cause molecular vibration.

The results of the foregoing examination suggest that electron transfer agents suitable for photoreceptors should require strong molecular vibration to obtain electron transfer by proximity effect.

However, electrophotographic photoreceptors using said compound can not actually reach the sensitivity and residual potential of negatively charged electrophotographic photoreceptors on the market, and further studies are needed to enhance molecular vibration in electron transfer agents.

DISCLOSURE OF THE INVENTION

In order to solve such problems of the prior art, an object of the present invention is to provide an electrophotographic photoreceptor which is excellent in sensitivity and residual potential and to provide a novel and useful electron transfer agent which can be dispersed in a photosensitive layer at a high concentration and which can be molecularly designed to have a desired magnitude of molecular vibration.

In order to attain the above object, the invention of claim 1 provides an electrophotographic photoreceptor comprising an organic thin film formed on a conductive substrate, characterized in that said organic thin film contains a compound of the following general formula (1):

(1)

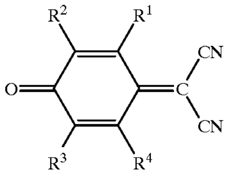

wherein $R^1$ represents either a non-cyclic saturated hydrocarbon or a cyclic saturated hydrocarbon, $R^2$ and $R^3$ represent any one of a cyano group, a nitro group, a halogen, a heterocycle, a non-cyclic hydrocarbon, a cyclic saturated hydrocarbon, an alkoxy group of a non-cyclic hydrocarbon or an alkoxy group of a cyclic saturated hydrocarbon, $R^4$ represents any one of a hydrogen, a non-cyclic saturated hydrocarbon or a cyclic saturated hydrocarbon, provided that any two of $R^1$, $R^2$, $R^3$ and $R^4$ may be the same or all of them may be different, and each of $R^1$, $R^2$, $R^3$ and $R^4$ itself may have a substituent unless it represents a hydrogen, a cyano group, a nitro group or a halogen element.

Our invention of electrophotographic photoreceptors containing said compound and compounds of special utility for them has the following history.

On the assumption that a substituent other than hydrogen for $R^1$ in general formula (1) increases molecular vibration when electrons are given, we examined the stereostructure of compounds of the following formulae (2) and (3):

(2)

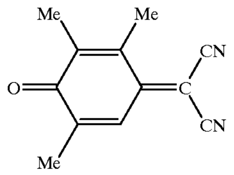

(3)

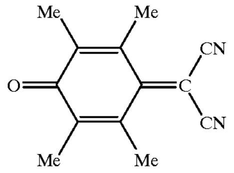

by introducing a methyl group into $R^1$–$R^3$ and a hydrogen atom into $R^4$ or a methyl group into $R^1$–$R^4$.

FIGS. 3*a*, 3*b*, 3*c* and FIGS. 4*a*, 4*b*, 4*c* show that the rings are more strained in the neutral state and that, when one or two electrons were given, the rings changed into a plane and a significant torsion occurred in the dicyanomethylene group, as compared with FIGS. 1*a*, 1*b*, 1*c* and FIGS. 2*a*, 2*b*, 2*c*.

This proved that a substituent other than hydrogen for $R^1$ in general formula (1) increases molecular vibration.

When a compound of the following formula (4):

(4)

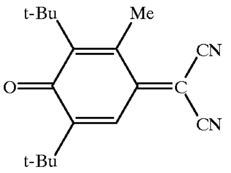

was also examined by introducing a methyl group into $R^1$ to increase molecular vibration, a bulky substituent tBu group into $R^2$ and $R^3$, and a hydrogen into $R^4$, it was observed that the ring is further strained in the neutral state to further increase molecular vibration, as shown in FIGS. 5*a*, 5*b*, 5*c*. This compound was confirmed to be a novel compound since no CAS registration number has been assigned.

Thus, compounds of the present invention not only show high electron mobility but also can be theoretically molecularly designed for necessary functions as materials used in electrophotographic photoreceptors. Any electron transfer agent incorporating such well-defined and specific molecule-designing means has not been known, and compounds of the present invention are electron transfer agents which can solve all the previous problems and which are very useful for use in electrophotographic photoreceptors.

BRIEF DESCRIPTION OF THE DRAWINGS

Preferred embodiments of electrophotographic photoreceptors according to the present invention will now be described in detail with reference to the accompanying drawings wherein.

THE MOST PREFERRED EMBODIMENTS OF THE INVENTION

Figure 1A:
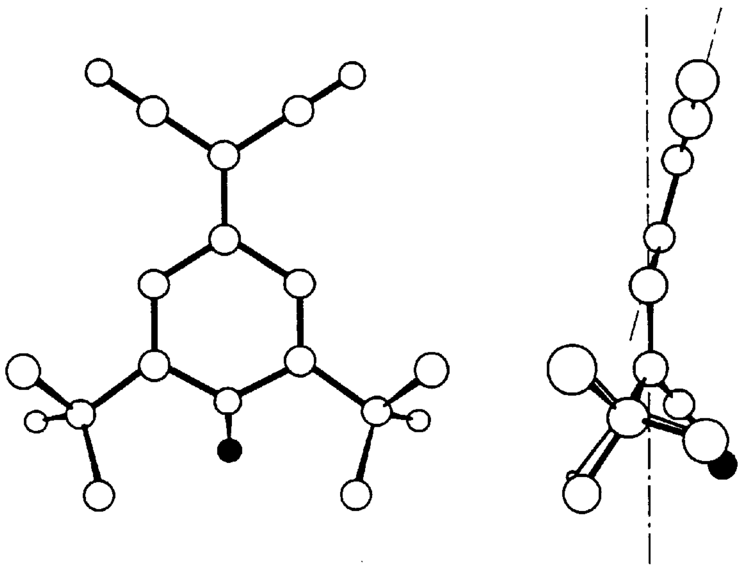
Fig. 1a PRIOR ART
FIG. 1*a* is a diagram for illustrating the molecular structure of the compound of chemical formula (5) in the neutral state.
Figure 1B:
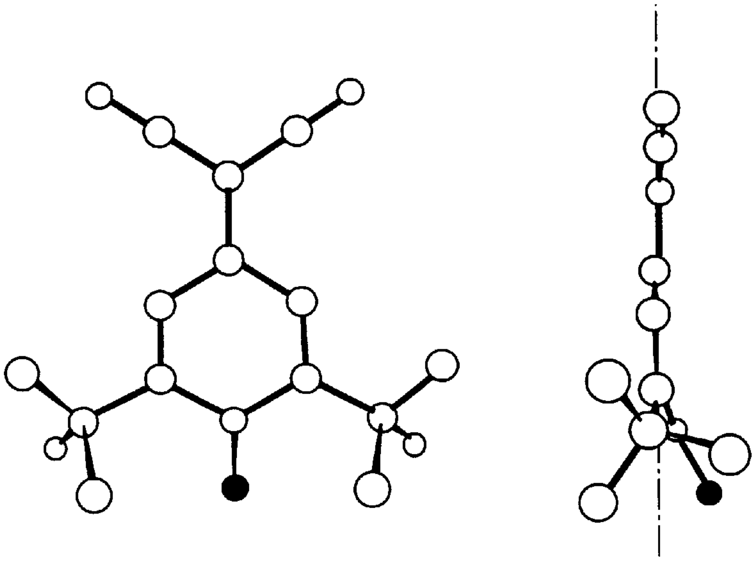
Fig. 1b PRIOR ART
FIG. 1*b* is a diagram for illustrating the molecular structure of the compound of chemical formula (5) to which one electron has been given.
Figure 1C:
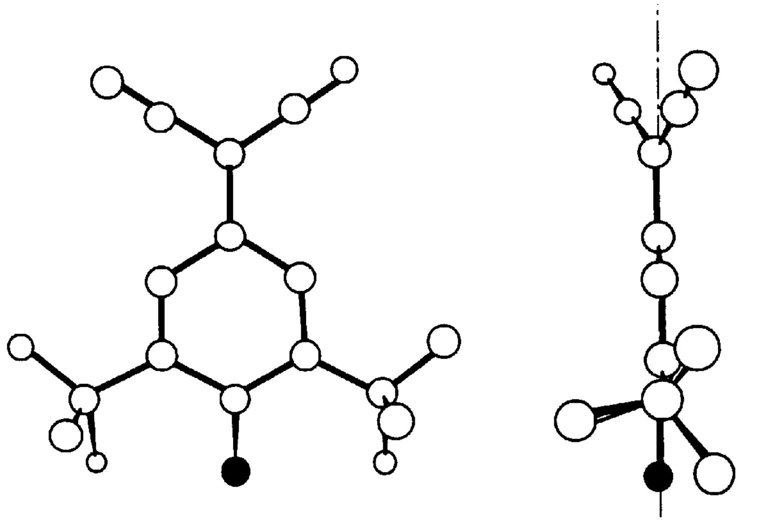
Fig. 1c PRIOR ART
FIG. 1*c* is a diagram for illustrating the molecular structure of the compound of chemical formula (5) to which two electrons have been given.
Figure 2C:
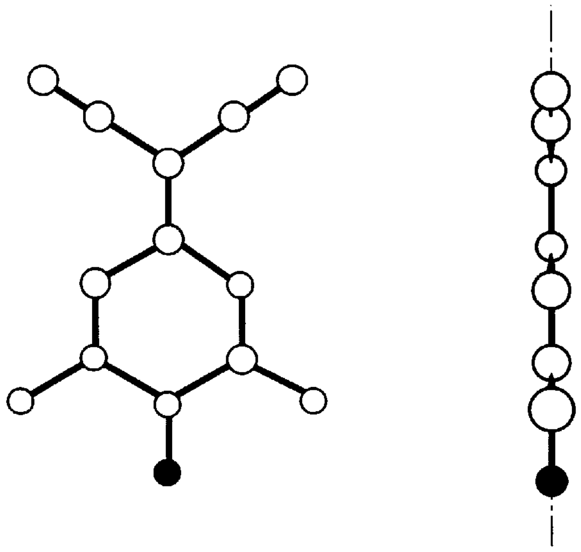
Fig. 2c PRIOR ART
FIG. 2*c* is a diagram for illustrating the molecular structure of the compound of chemical formula (6) to which two electrons have been given.
Figure 2B:
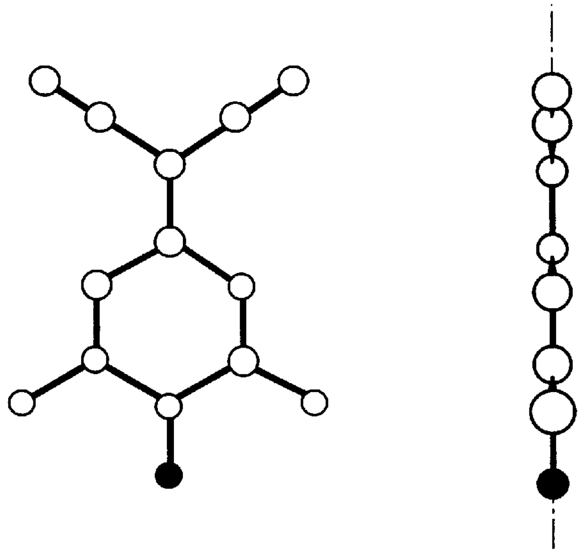
Fig. 2b PRIOR ART
FIG. 2*b* is a diagram for illustrating the molecular structure of the compound of chemical formula (6) to which one electron has been given.
Figure 2A:
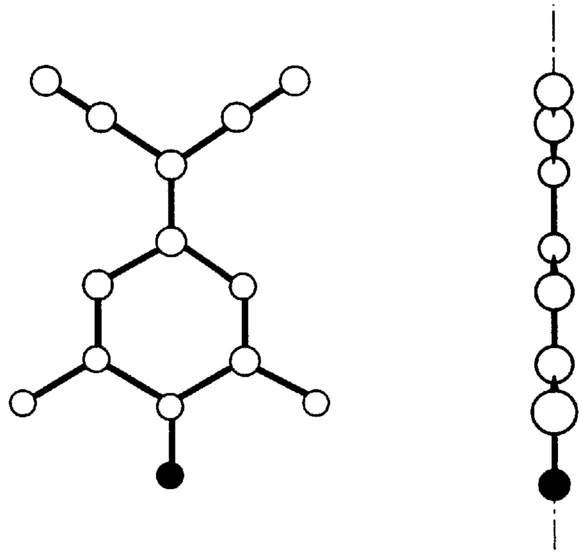
Fig. 2a PRIOR ART
FIG. 2*a* is a diagram for illustrating the molecular structure of the compound of chemical formula (6) in the neutral state.
Figure 3C:
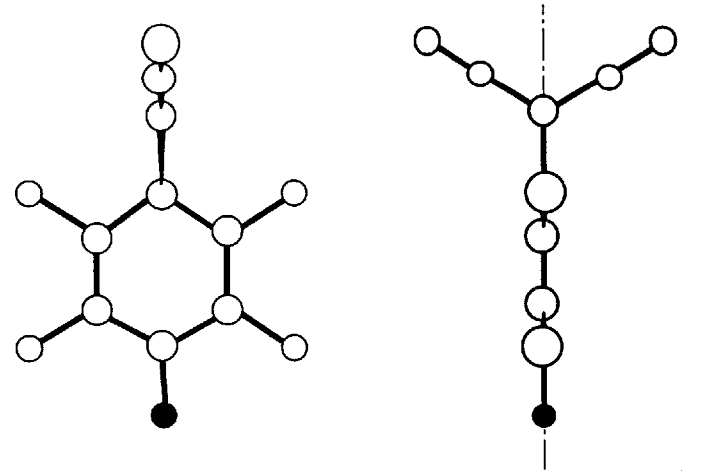
FIG. 3*c* is a diagram for illustrating the molecular structure of the compound of chemical formula (3) to which two electrons have been given.
Figure 3B:
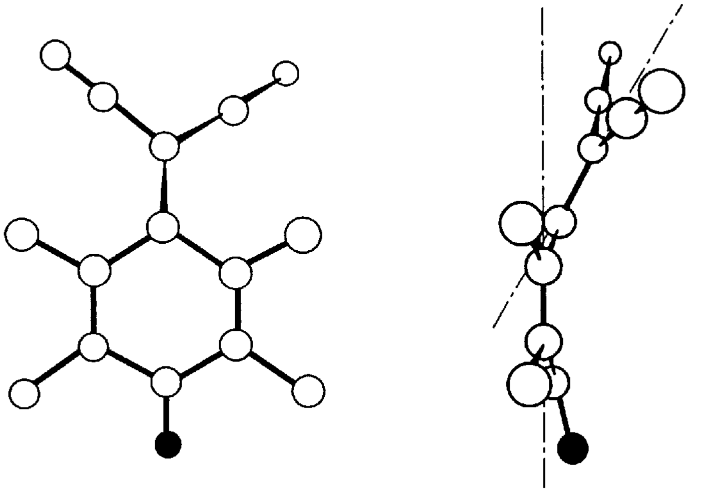
FIG. 3*b* is a diagram for illustrating the molecular structure of the compound of chemical formula (3) to which one electron has been given.
Figure 3A:
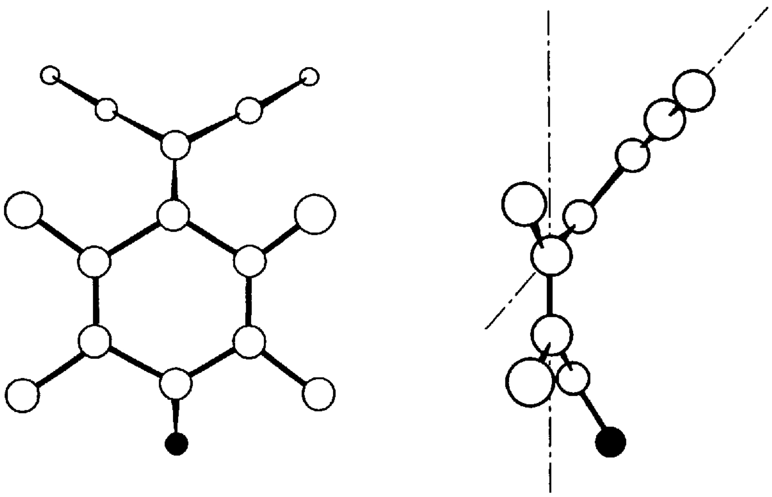
FIG. 3*a* is a diagram for illustrating the molecular structure of the compound of chemical formula (3) in the neutral state.
Figure 4A:
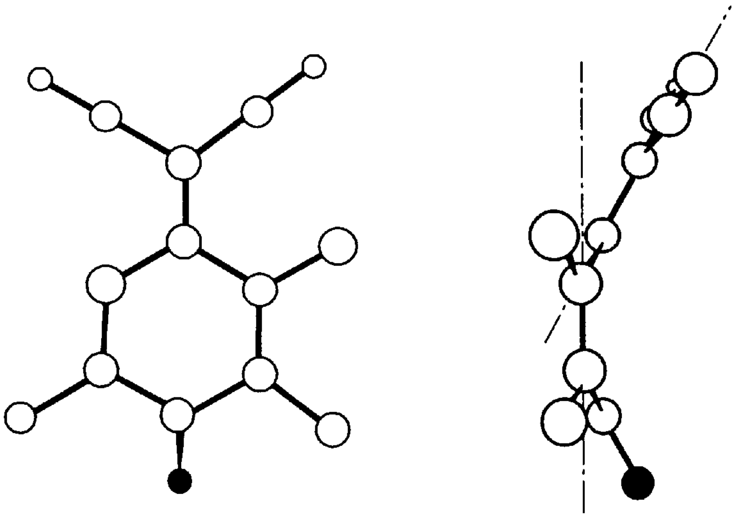
FIG. 4*a* is a diagram for illustrating the molecular structure of the compound of chemical formula (2) in the neutral state.
Figure 4B:
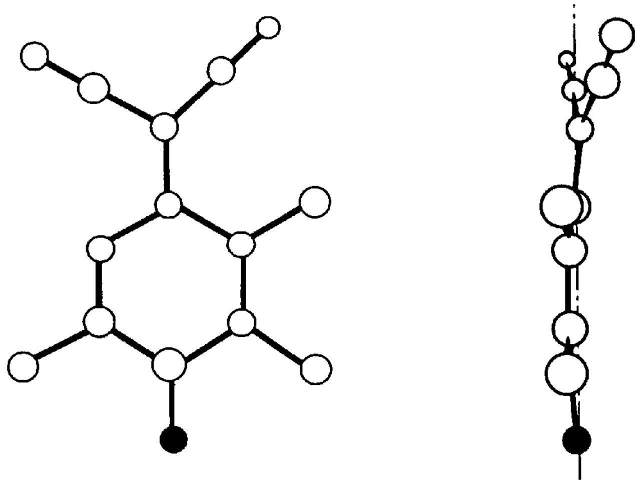
FIG. 4*b* is a diagram for illustrating the molecular structure of the compound of chemical formula (2) to which one electron has been given.
Figure 4C:
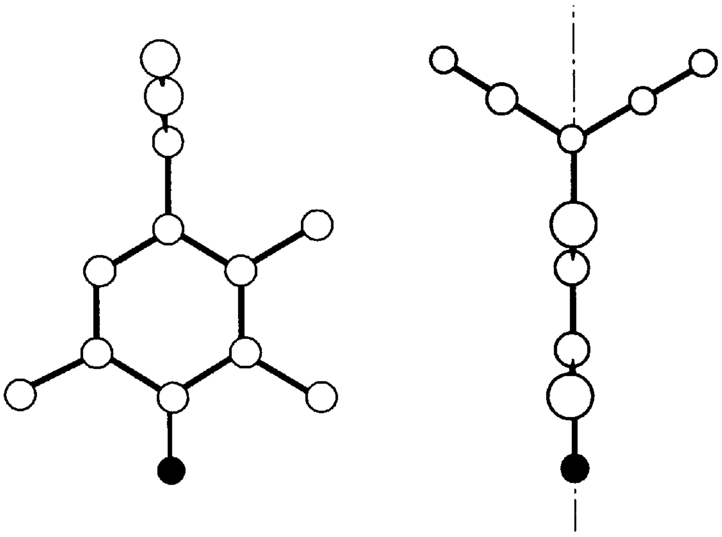
FIG. 4*c* is a diagram for illustrating the molecular structure of the compound of chemical formula (2) to which two electrons have been given.
Figure 5C:
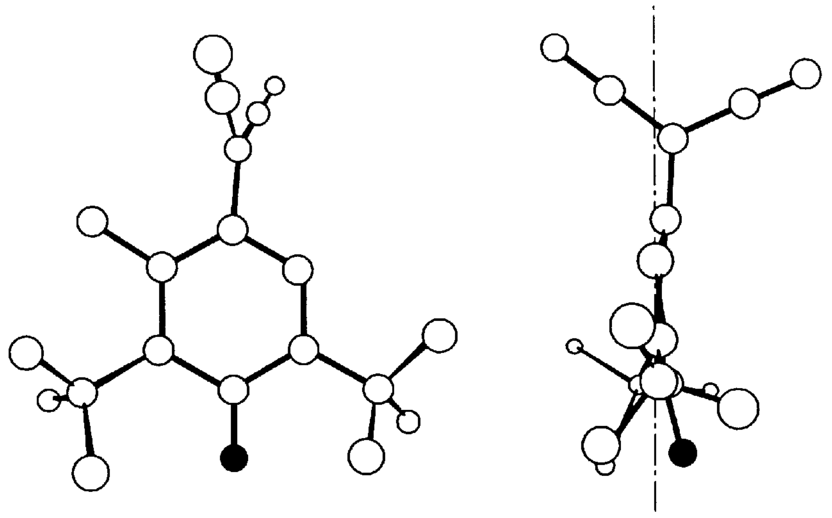
FIG. 5*c* is a diagram for illustrating the molecular structure of the compound of chemical formula (4) to which two electrons have been given.
Figure 5B:
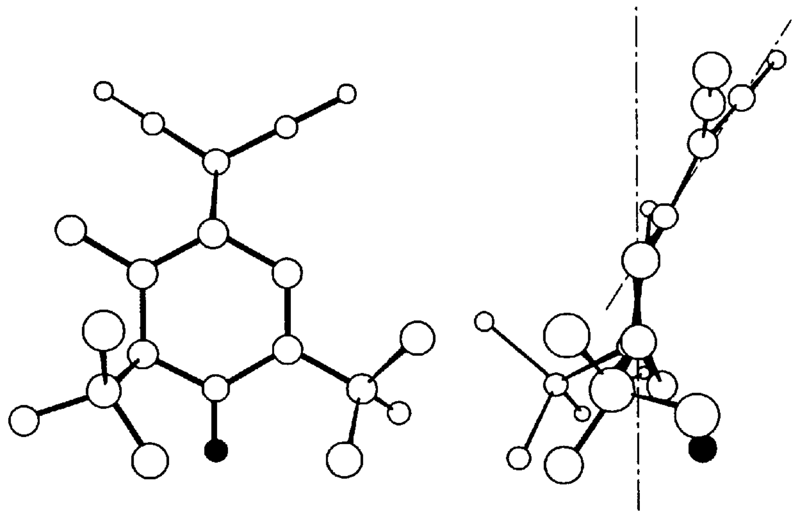
FIG. 5*b* is a diagram for illustrating the molecular structure of the compound of chemical formula (4) to which one electron has been given.
Figure 5A:
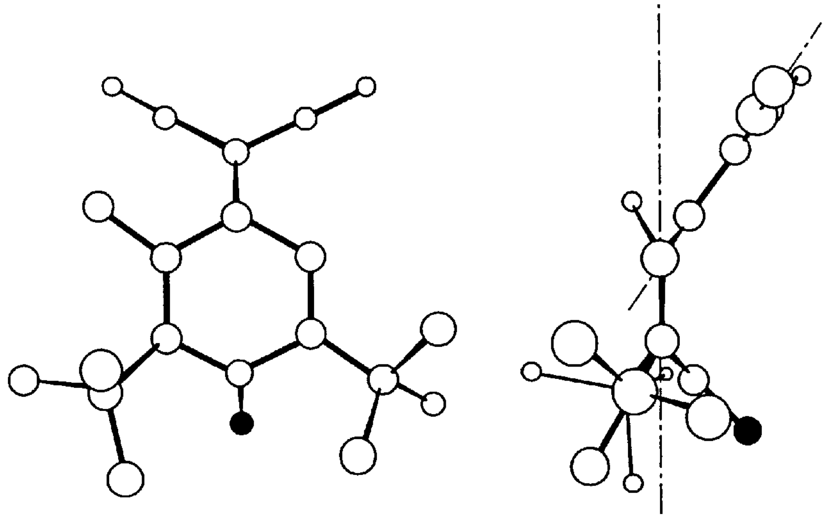
FIG. 5*a* is a diagram for illustrating the molecular structure of the compound of chemical formula (4) in the neutral state.
Figure 6:
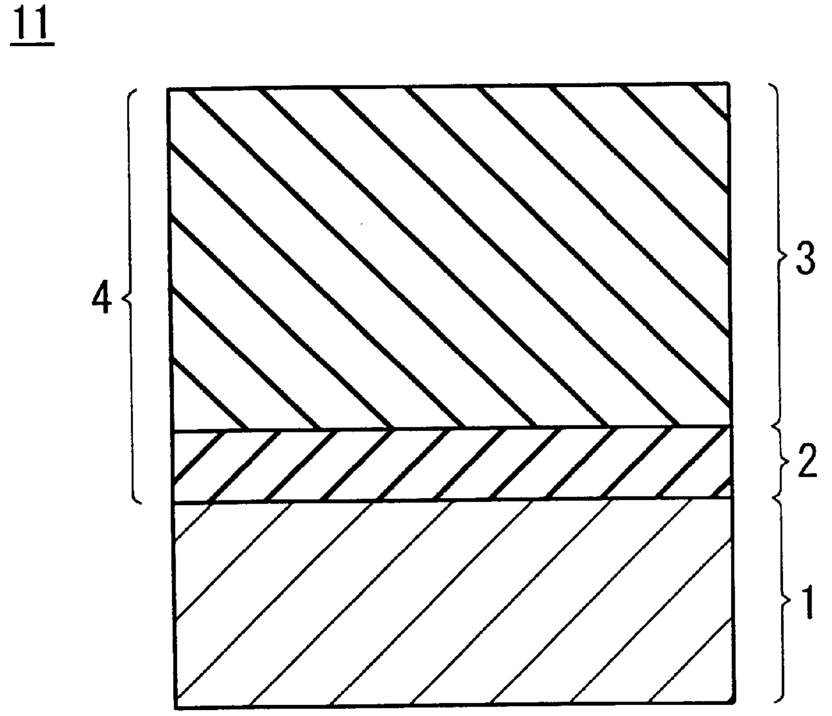
FIG. 6 is a sectional view showing an example of the multilayer type electrophotographic photoreceptor.
Figure 7:
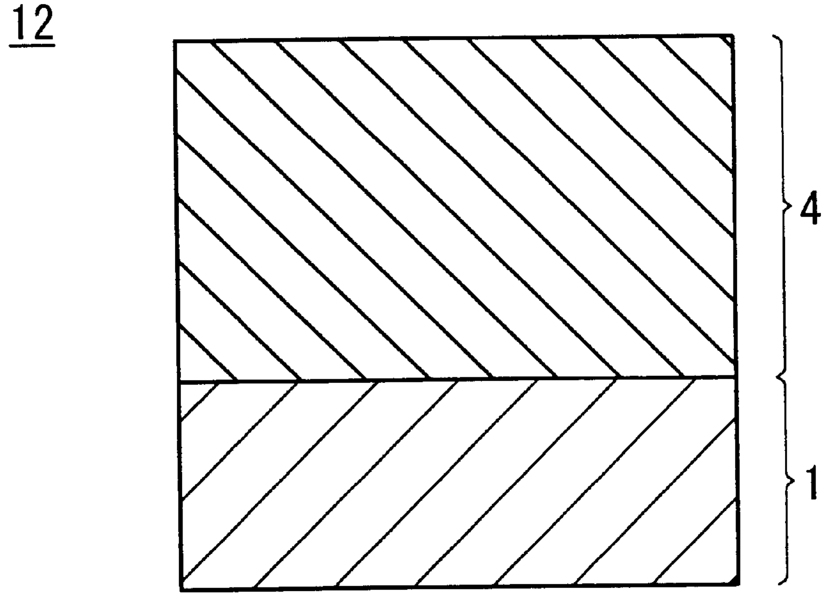
FIG. 7 is a sectional view showing an example of the monolayer type electrophotographic photoreceptor.
Figure 8:
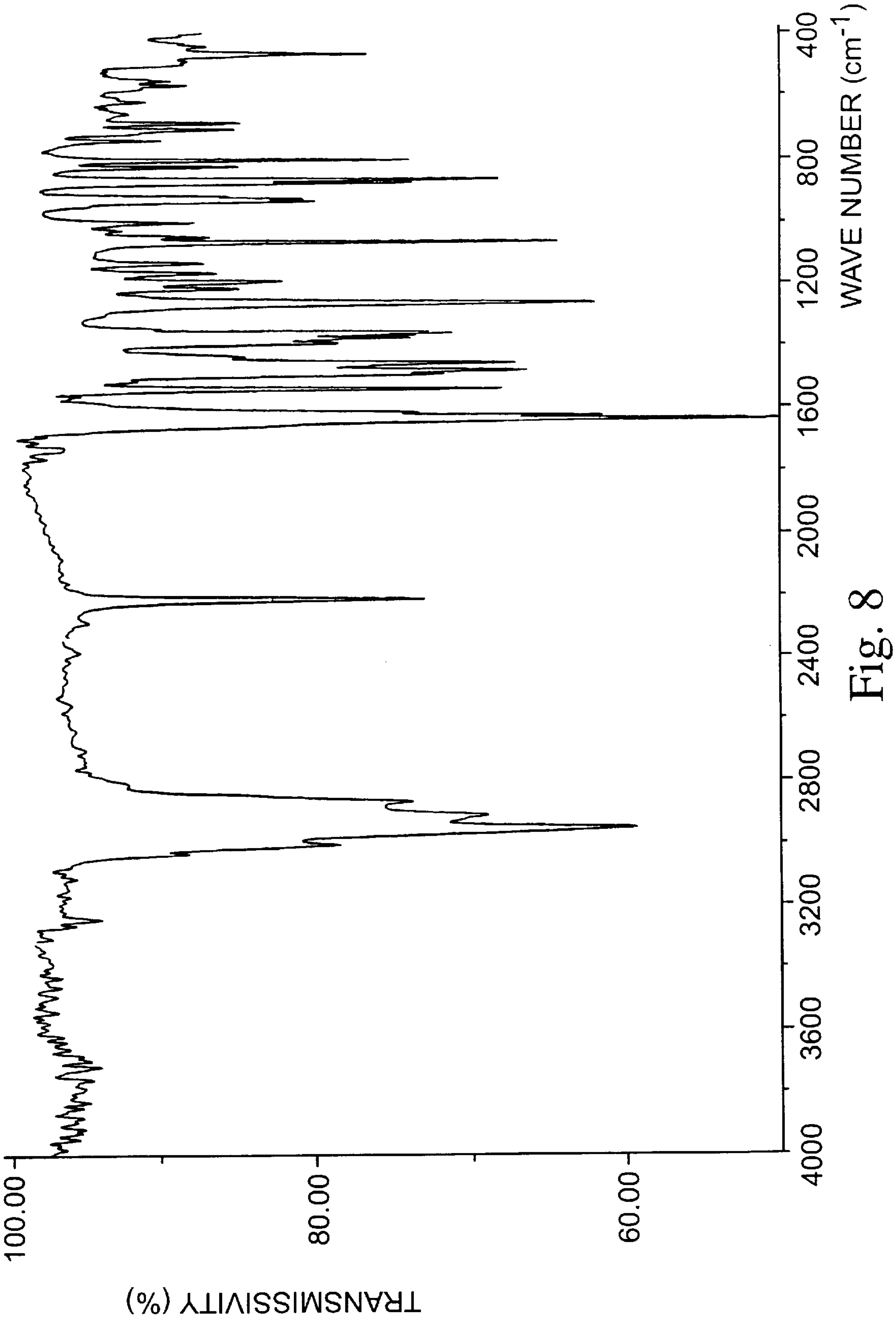
FIG. 8 is an IR spectral chart of the compound of general formula (4)
Figure 9:
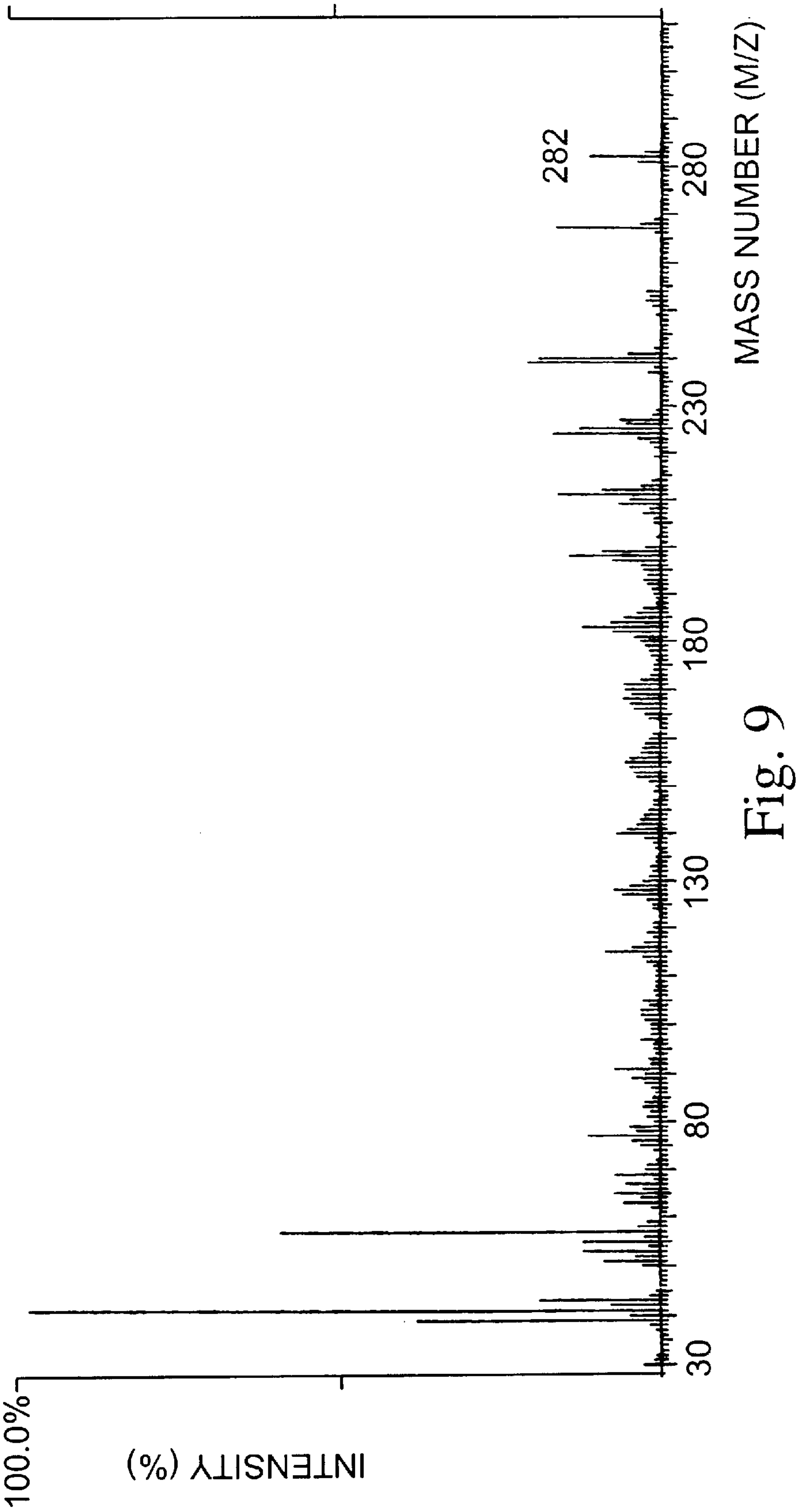
FIG. 9 is an MS spectral chart of the compound of general formula (4)
Figure 10:
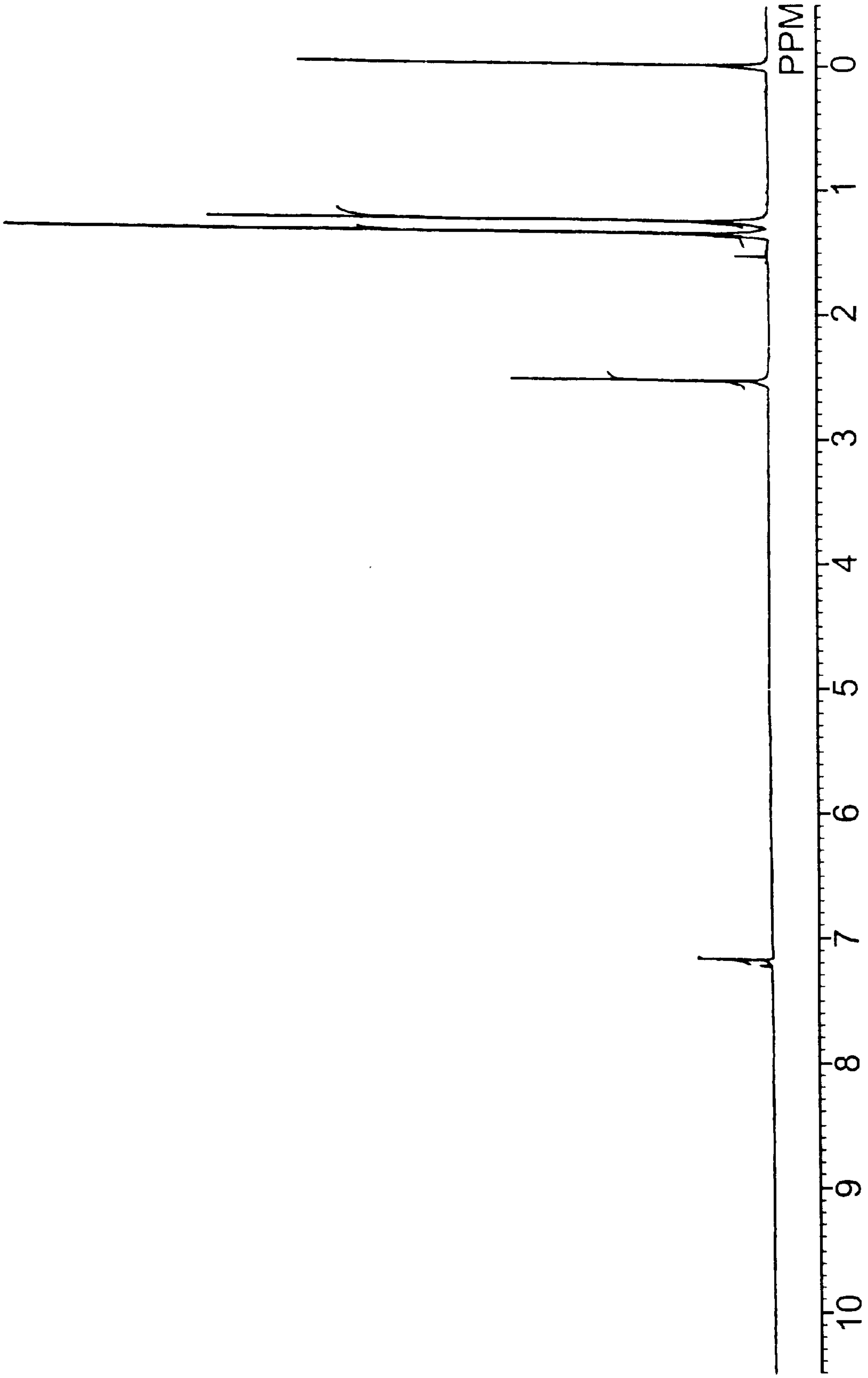
FIG. 10 is a $^1$H-NMR spectral chart of the compound of general formula (4)
Figure 11:
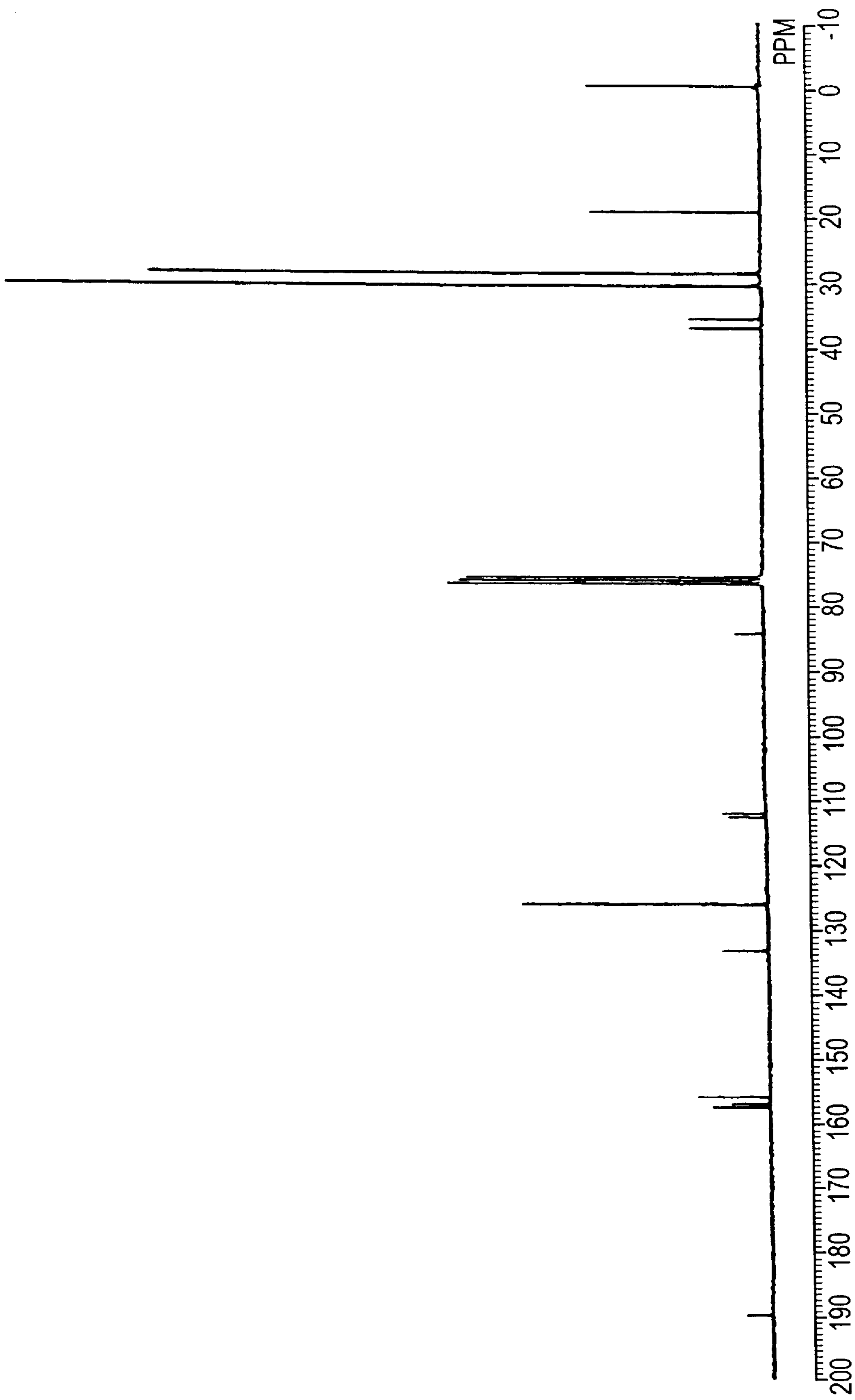
FIG. 11 is a $^{13}$C-NMR spectral chart of the compound of general formula (4)

Numeral reference 11 in FIG. 6 and numeral reference 12 in FIG. 7 represent examples of electrophotographic photoreceptors according to the present invention, of which the electrophotographic photoreceptor 11 is a function-separated type and the electrophotographic photoreceptor 12 is a monolayer-dispersed type, and both electrophotographic photoreceptors 11, 12 are embodiments using an organic thin film containing a compound of the present invention as a photosensitive layer.

The electrophotographic photoreceptor 11 shown in FIG. 6 comprises a carrier generation layer 2 and a carrier transport layer 3 successively formed on a cylindrical conductive substrate 1, so that a photosensitive layer 4 consists of said carrier generation layer 2 and carrier transport layer 3.

The carrier generation layer 2 shown in FIG. 6 has at least a carrier generation material and can be formed by securing the carrier generation material on the underlying conductive substrate 1 with a binder resin.

The carrier generation layer 2 can be formed by using various methods such as known methods, for example, by applying a coating fluid containing a carrier generation material with a binder resin dispersed or dissolved in an appropriate solvent on a predetermined underlying conductive substrate 1 and drying it.

The carrier generation layer 2 can also be formed by vapor-depositing a carrier generation material in vacuo.

The carrier transport layer 3 has at least a carrier transport material described later, and can be formed by securing the carrier transport material on the underlying carrier generation layer 2 with a binder resin.

The carrier transport layer 3 can be formed by using various methods such as known methods, ordinarily by applying a coating fluid containing a carrier transport material with a binder resin dispersed or dissolved in an appropriate solvent on a predetermined underlying carrier generation layer 2 and drying it.

Numeral reference 12 in FIG. 7 represents a monolayer type electrophotographic photoreceptor according to another embodiment of the present invention, wherein a monolayer photosensitive layer 4 containing a carrier generation material and a carrier transport material is formed on a conductive substrate 1, as designated with the same references as used for similar elements of the electrophotographic photoreceptor 11 according to the above first embodiment of the present invention.

The photosensitive layer 4 can be formed by using various methods such as known methods, for example, by applying a coating fluid containing a carrier generation material described later with a binder resin dispersed or dissolved in an appropriate solvent and further containing a carrier transport material dissolved therein on a predetermined underlying conductive substrate 1 and drying it.

The conductive substrate 1 suitable for the present invention can be made of various conductive materials, without limited to any nature or shape, including processed articles of elementary metals such as aluminium, magnesium, brass, stainless steel, nickel, chromium, titanium, gold, silver, copper, tin, platinum, molybdenum, indium or alloys thereof; plastic boards or films on which a conductive material such as said metals or carbon has been vapor-deposited or plated to render them conductive; or conductive glasses coated with tin oxide, indium oxide, aluminium iodide or copper iodide.

Generally, cylindrical aluminium tubes alone, with deposited aluminum oxide layer thereover, or coated with a resin layer thereon are commonly used. This resin layer has functions to improve adhesion, block inflow current from the substrate, cover defects on the surface of the substrate, etc. This resin layer may be made of various resins such as polyethylene resins, acrylic resins, epoxy resins, polycarbonate resins, polyurethane resins, vinyl chloride resins, vinyl acetate resins, polyvinyl butyral resins, polyamide resins, nylon resins, etc. These resin layers may be made of a single resin or a mixture of two or more resins. Furthermore, the resin layer may contain metal compounds, metal oxides, carbon, silica, resin powder or the like dispersed therein. Various pigments, electron-accepting substances or electron-donating substances or the like may also be contained to improve characteristics.

Current generation materials suitable for the present invention are desirably, but not limited to, disazo pigments and oxytitanium phthalocyanine because of their good compatibility of sensitivity. Other examples include, for instance, selenium, selenium-tellurium, selenium-arsenic, amorphous silicon, phthalocyanine pigments, monoazo pigments, trisazo pigments, polyazo pigments, indigo pigments, toluidine pigments, pyrazoline pigments, perylene pigments, quinacridone pigments, pyrylium salts, etc.

These carrier generation materials may be used alone or as a mixture of two or more to obtain suitable photosensitivity wavelength or sensitizing effects.

Binder resins suitable for forming the photosensitive layer 4 are photo-setting resins such as polycarbonate resins, styrene resins, acrylic resins, styrene-acrylic resins, ethylene-vinyl acetate resins, polypropylene resins, vinyl chloride resins, chlorinated polyethers, vinyl chloride-vinyl acetate resins, polyester resins, furan resins, nitrile resins, alkyd resins, polyacetal resins, polymethylpentene resins, polyamide resins, polyurethane resins, epoxy resins, polyallylate resins, diallylate resins, polysulfone resins, polyethersulfone resins, polyallysulfone resins, silicone resins, ketone resins, polyvinyl butyral resins, polyether resins, phenol resins, EVA (ethylene-vinyl acetate copolymer) resins, ACS (acrylonitrile-chlorinated polyethylene-styrene) resins, ABS (acrylonitrile-butadiene-styrene) resins, epoxyallylates, etc. These may be used alone or as a copolymer or a mixture of two or more. It is preferable to use a mixture of resins with different molecular weights to improve hardness or resistance to wear. Said binder resins may be used in any of the carrier generation layer 2 and the carrier transport layer 3 in the function-separated type photoreceptor shown in FIG. 7.

Solvents used in the coating fluid include alcohols such as methanol, ethanol, n-propanol, iso-propanol, butanol; saturated aliphatic hydrocarbons such as pentane, hexane, heptane, octane, cyclohexane, cycloheptane; aromatic hydrocarbons such as toluene, xylene; chlorine-based hydrocarbons such as dichloromethane, dichloroethane, chloroform, chlorobenzene; ethers such as dimethylether, diethylether, tetrahydrofuran (THF), methoxyethanol; ketones such as acetone, methyl ethyl ketone, methyl isobutyl ketone, cyclohexanone; esters such as ethyl formate, propyl formate, methyl acetate, ethyl acetate, propyl acetate, butyl acetate, methyl propionate; N,N-dimethylformamide; dimethyl sulfoxide, etc. These may be used alone or as a mixture of two or more solvents.

Electrophotographic photoreceptors according to the present invention contain a compound of the following general formula (1) as a carrier transport material in the photosensitive layer 4:

(1)

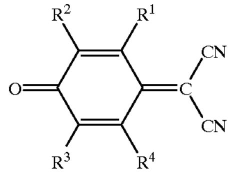

wherein $R^1$ represents either a non-cyclic saturated hydrocarbon or a cyclic saturated hydrocarbon, $R^2$ and $R^3$ represent any one of a cyano group, a nitro group, a halogen, a heterocycle, a non-cyclic hydrocarbon, a cyclic saturated hydrocarbon, an alkoxy group of a non-cyclic hydrocarbon or an alkoxy group of a cyclic saturated hydrocarbon, $R^4$ represents any one of a hydrogen, a non-cyclic saturated hydrocarbon or a cyclic saturated hydrocarbon, provided that any two or more of $R^1$, $R^2$, $R^3$ and $R^4$ may be the same or all of them may be different, and each of $R^1$, $R^2$, $R^3$ and $R^4$ itself may have a substituent unless it represents a hydrogen, a cyano group, a nitro group or a halogen element.

This compound preferably has a substituent other than hydrogen for $R^1$ and a substituent other than hydrogen for at least two of $R^2$–$R^4$, more preferably an alkyl group for $R^2$–$R^4$, and the compound is preferably represented by the following chemical formula (2) or (3), especially preferably (4):

(2)

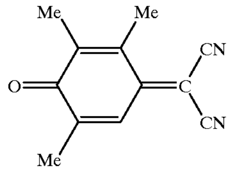

(3)

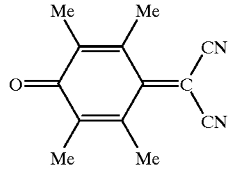

(4)

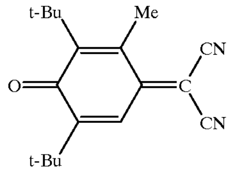

Electrophotographic photoreceptors according to the present invention may further contain other carrier transport materials. Such materials can enhance sensitivity or lower residual potential to improve characteristics of electrophotographic photoreceptors of the present invention.

Such carrier transport materials which may be added to improve characteristics include conductive polymer compounds such as polyvinyl carbazole, halogenated polyvinyl carbazole, polyvinyl pyrene, polyvinyl indoloquinoxaline, polyvinyl benzothiophene, polyvinyl anthracene, polyvinyl acrydine, polyvinyl pyrazoline, polyacetylene, polythiophene, polypyrrol, polyphenylene, polyphenylene vinylene, polyisothianaphthene, polyaniline, polydiacetylene, polyheptadiene, polypyridinediyl, polyquinoline, polyphenylene sulfide, polyferrocenylene, polyperinaphthylene, polyphthalocyanine etc. Low-molecular weight compounds may also be used including trinitrofluorenone, tetracyanoethylene, tetracyanoquinodimethane, quinone, diphenoquinone, naphthoquinone, anthraquinone and derivatives thereof; polycyclic aromatic compounds such as anthracene, pyrene, phenanthrene; nitrogen-containing heterocyclic compounds such as indole, carbazole, imidazole etc.; fluorenone, fluorene, oxadiazole, oxazole, pyrazoline, hydrazone, triphenylmethane, triphenylamine, enamine, stilbene, butadiene compounds etc.

Polymer solid electrolytes comprising a polymer compound such as polyethylene oxide, polypropylene oxide, polyacrylonitrile, polymethacrylic acid doped with a metal ion such as Li ion may also be used.

Organic carrier transport complexes formed of an electron-donating compound and an electron-accepting compound represented by tetrathiafulvalene-tetracyanoquinodimethane may also be used alone or as a mixture of two or more to obtain desired photosensitive characteristics.

So far as characteristics of electrophotographic receptors are not impaired, coating fluids for preparing photoreceptors of the present invention may contain antioxidants, ultraviolet absorbers, radical scavengers, softeners, curing agents, crosslinkers or the like to improve photosensitive characteristics, durability or mechanical properties.

Furthermore, dispersion stabilizers, anti-setting agents, anti-segregating agents, leveling agents, anti-foaming agents, thickeners, matting agents, etc. may also be added to improve finished appearance of photoreceptors or lifetime of coating fluids.

A surface protective layer may be further applied on the photosensitive layer 4 by forming an organic thin film from epoxy resins, melamine resins, polyvinyl formal resins, polycarbonate resins, fluorine resins, polyurethane resins, silicone resins or the like; or a thin film of a siloxane structure from a hydrolyzate of a silane-coupling agent. This preferably improves durability of the photoreceptor. This surface protective layer may be applied to improve other functions than durability.

The following examples illustrate electrophotographic photoreceptors according to the present invention in detail.

At first, examples of the process for preparing compounds of the above general formula (1) is described.

PREPARATION EXAMPLE 1

Under a nitrogen atmosphere, 0.20 ml of malononitrile was added to a solution of 0.44 g of tetramethyl-p-benzoquinone in 25 ml of anhydrous dichloromethane, and a solution of 0.36 ml of titanium (IV) chloride in 10 ml of anhydrous dichloromethane was added dropwise to the mixed solution over 10 minutes with stirring at 0–5° C. and then 0.87 ml of anhydrous pyridine was added dropwise over 10 minutes. After stirred at room temperature for 15 hours, the reaction solution was washed three times with 30 ml of water to separate organic layers, which were dried over anhydrous sodium sulfate. The solution was concentrated under reduced pressure and separated by column chromatography (silica gel: developing solvent hexane/ethyl acetate=3/1) to give a crude crystal, which was then recrystallized from hexane to give 0.07 g of a yellow-orange needle crystal. The yield was 12%. This reaction is represented by the following reaction formula (7):

(7)

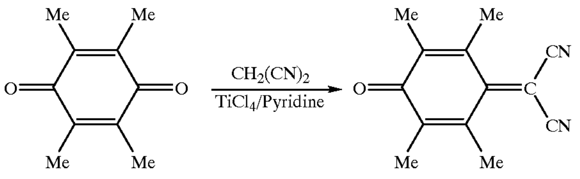

The product was identified as 2,3,5,6-tetramethyl-4-oxo-2,5-cyclohexadiene-1-ylidenepropanedinitrile represented by chemical formula (3) from the following analysis data.

m.p.: 130–135° C. IR (KBr): 690, 775, 1265, 1385, 1510, 1630 (C═O), 2225, 2970, 2995, 3235 $cm^{-1}$. $^1$H-NMR ($CDCl_3$) δ: 2.02 (s, 6H, $CH_3$), 2.44 (s, 6H, $CH_3$). MS (m/z): 212 ($M^+$). (Molecular weight: 212.25).

PREPARATION EXAMPLE 2

To a solution of 2.0 g of trimethylhydroquinone in 300 ml of chloroform was added 10 g of lead (IV) oxide, and the mixed solution was stirred at room temperature for 30 hours and then lead (IV) oxide was filtered off and the reaction solution was concentrated under reduced pressure. The concentrate was combined with 150 ml of hexane, washed with 50 ml of a 0.5% sodium bicarbonate solution and then 50 ml of water, dried over anhydrous sodium sulfate, then concentrated under reduced pressure. After cooling in a freezer, the precipitating crystal was filtered and washed with a small amount of cold hexane to give 2,3,5-trimethylbenzoquinone as a yellow needle crystal. The yield was 1.6 g (82%).

Then, 0.42 ml of malononitrile was added to a solution of 0.41 g of 2,3,5-trimethylbenzoquinone in 25 ml of anhydrous dichloromethane under a nitrogen atmosphere, and a solution of 0.74 ml of titanium (IV) chloride in 25 ml of anhydrous dichloromethane was added dropwise to the mixed solution over 15 minutes with stirring at 0–5° C. and then 1.08 ml of anhydrous pyridine was added dropwise over 10 minutes. After stirred at room temperature for 15 hours, the reaction solution was washed four times with 50 ml of water to separate organic layers, which were dried over anhydrous sodium sulfate. The solution was concentrated under reduced pressure and separated by column chromatography (silica gel: developing solvent hexane/ethyl acetate=6/1) to give a crude crystal, which was then recrystallized from hexane to give 0.17 g of an orange needle crystal. The yield was 32%. This reaction is represented by the following reaction formula (8):

(8)

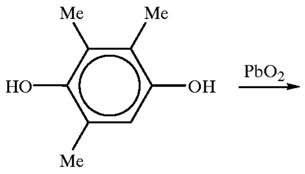

-continued

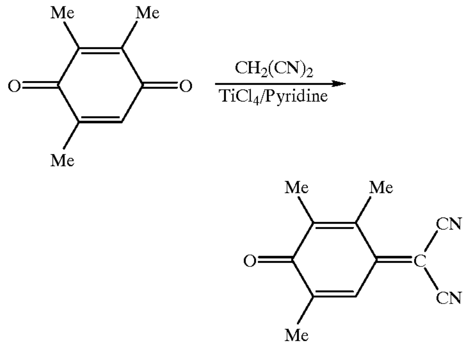

The product was identified as 2,3,5-trimethyl-4-oxo-2,5-cyclohexadiene-1-ylidenepropanedinitrile represented by chemical formula (2) from the following analysis data.

m.p.: 104–105° C. IR (KBr): 670, 780, 875, 1285, 1580, 1630 (C═O), 2225, 2930, 2960, 3235 $cm^{-1}$. $^1$H-NMR ($CDCl_3$) δ: 2.12 (s, 6H, $CH_3$), 2.52 (s, 3H, $CH_3$), 7.46 (s, 1H, aromatic H). MS (m/z): 198 ($M^+$). (Molecular weight: 198.23).

PREPARATION EXAMPLE 3

To a solution of 5.0 g of 2,6-di-t-butyl-p-cresol in 90 ml of acetonitrile/water (5/1) was added 10.5 g of bistrifluoroacetoxyiodobenzene with stirring at 0° C. After stirring for 30 minutes, 90 ml of water was added and the reaction solution was extracted three times with 50 ml of dichloromethane and washed four times with 60 ml of water. Organic layers were dried over anhydrous sodium sulfate, then concentrated under reduced pressure and the precipitating crystal was filtered to give a crude crystal, which was recrystallized from hexane to give 4-methyl-4-hydroxy-2,6-di-t-butylcyclohexa-2,5-diene-1-one as a pale yellow solid. The yield was 3.0 g (55%).

Then, 1.2 g of potassium t-butoxide and 30 ml of N,N-dimethylformamide were stirred at room temperature for 5 minutes under a nitrogen atmosphere, and then further stirred with 0.9 g of 4-methyl-4-hydroxy-2,6-di-t-butylcyclohexa-2,5-diene-1-one for 3 hours, then the reaction solution was poured on a mixture of 60 g of ice and 1 ml of concentrated hydrochloric acid.

The reaction solution was extracted 5 times with 60 ml of hexane, and the extracts were washed with 60 ml of water and then dried over anhydrous sodium sulfate. Organic layers were concentrated under reduced pressure and the concentrate was separated by column chromatography (silica gel: developing solvent hexane/dichloromethane=1/2) to give 2,6-di-t-butyl-3-methyl-p-benzoquinone as an orange oil. The yield was 0.7 g (81%).

Finally, 0.42 ml of malononitrile was added to a solution of 0.63 g of 2,6-di-t-butyl-3-methyl-p-benzoquinone in 25 ml of dichloromethane under a nitrogen atmosphere, and a solution of 0.74 ml of titanium (IV) chloride in 25 ml of dichloromethane was added dropwise to the mixed solution over 20 minutes with stirring at 0–5° C. and then 1.08 ml of pyridine was added dropwise over 10 minutes. After stirred at room temperature overnight, the reaction solution was washed four times with 50 ml of water to separate organic layers, which were dried over anhydrous sodium sulfate. The solution was concentrated under reduced pressure and separated by column chromatography (silica gel: developing solvent hexane/ethyl acetate=30/1) to give a crude crystal, which was then recrystallized from hexane to give 0.39 g of a red plate crystal. The yield was 51%. This reaction is represented by the following reaction formula (9):

(9)

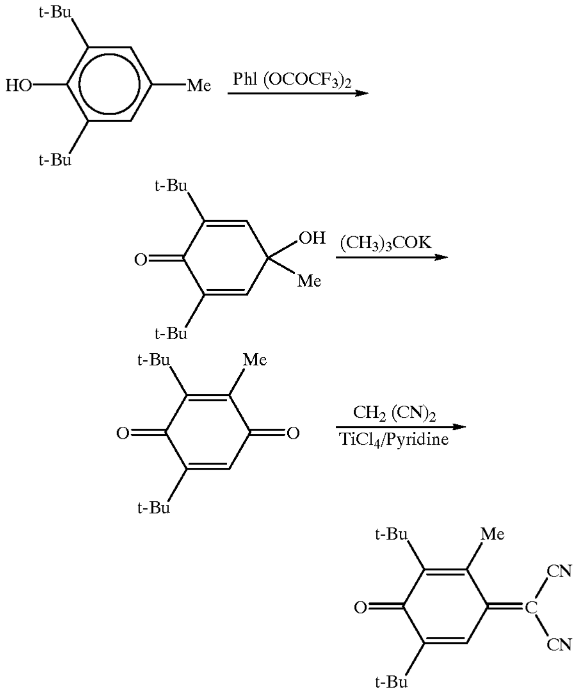

The product was identified as 3,5-di-t-butyl-2-methyl-4-oxo-2,5-cyclohexane-1-ylidenepropanedinitrile represented by chemical formula (4) from the following analysis data.

m.p.: 87.5–88.5° C. IR (KBr) : 470, 875, 1070, 1265, 1460, 1485, 1545, 1645 (C═O), 2220, 2960 $cm^{-1}$. $^1$H-NMR ($CDCl_3$) δ: 1.29 (s, 9H, tert-Bu), 1.38 (s, 9H, tert-Bu), 2.56 (s, 3H, $CH_3$), 7.21 (s, 1H, aromatic H). $^{13}$C-NMR ($CDCl_3$) δ: 19.80, 29.14, 31.08, 35.99, 37.48, 85.21, 113.30, 113.86, 127.47, 134.69, 156.84, 157.90, 158.42, 190.30. MS (m/z): 282 ($M^+$). (Molecular weight: 282.38). Elementary analysis ($C_{18}H_{22}N_2O$): calculated: C76.6, H7.9, N9.9; found: C76.7, H7.9, N10.0.

The IR spectral chart, MS spectral chart, $^1$H-NMR spectral chart and $^{13}$C-NMR spectral chart of the compound of chemical formula (4) are shown in FIGS. 8, 9, 10 and 11, respectively.

Specific examples of electrophotographic photoreceptors according to the present invention are described below together with comparative examples, but the following examples are not construed as limiting the present invention without departing the spirit thereof.

EXAMPLE 1

After 2 parts by weight of a disazo pigment of the following chemical formula (10):

(10)

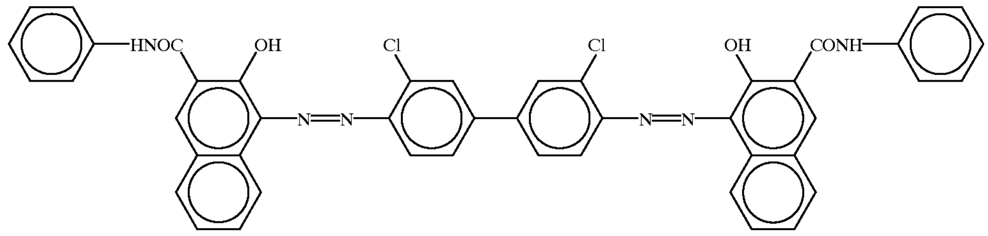

and 1 part by weight of a binder resin polyvinyl butyral were dry-blended, they were dispersed in a solvent consisting of 16 parts by weight of 1,4-dioxane and 4 parts by weight of acetone for 2 hours using a sand mill, and said dispersion was dip-coated on an aluminium drum forming a conductive substrate 1 and dried to form a carrier generation layer 2 having a thickness of 0.5 μm.

Then, a coating fluid was prepared from 8 parts by weight of the compound of the above chemical formula (2), 10 parts by weight of polycarbonate and 100 parts by weight of tetrahydrofuran (THF), and said coating fluid was dip-coated on the drum provided with the carrier generation layer 2 and dried at 80° C. for one hour to form a carrier transport layer 3 having a thickness of 20 μm, whereby an electrophotographic photoreceptor was prepared.

EXAMPLE 2

An electrophotographic photoreceptor was prepared in the same manner as described in Example 1 except that the compound of chemical formula (2) in the electrophotographic photoreceptor of Example 1 was replaced by the compound of chemical formula (3).

EXAMPLE 3

An electrophotographic photoreceptor was prepared in the same manner as described in Example 1 except that the compound of chemical formula (2) in the electrophotographic photoreceptor of Example 1 was replaced by the compound of chemical formula (4).

COMPARATIVE EXAMPLE 1

An electrophotographic photoreceptor was prepared in the same manner as described in Example 1 except that the compound of chemical formula (2) in the electrophotographic photoreceptor of Example 1 was replaced by the compound of chemical formula (5).

COMPARATIVE EXAMPLE 2

An electrophotographic photoreceptor was prepared in the same manner as described in Example 1 except that the compound of chemical formula (2) in the electrophotographic photoreceptor of Example 1 was replaced by the compound of chemical formula (6)

EXAMPLE 4

A carrier generation layer 2 was formed by vapor-depositing high-purity oxytitanyl phthalocyanine on an aluminium drum forming a conductive substrate 1 at a pressure of $10^{-5}$ torr and a heating temperature of 500° C. into a film thickness of 500 angstroms while a carrier transport layer 3 was formed in the same manner as described in Example 1 to prepare an electrophotographic photoreceptor.

EXAMPLE 5

An electrophotographic photoreceptor was prepared in the same manner as described in Example 4 except that the compound of chemical formula (2) in the electrophotographic photoreceptor of Example 4 was replaced by the compound of chemical formula (3).

EXAMPLE 6

An electrophotographic photoreceptor was prepared in the same manner as described in Example 4 except that the compound of chemical formula (2) in the electrophotographic photoreceptor of Example 4 was replaced by the compound of chemical formula (4).

COMPARATIVE EXAMPLE 3

An electrophotographic photoreceptor was prepared in the same manner as described in Example 4 except that the compound of chemical formula (2) in the electrophotographic photoreceptor of Example 4 was replaced by the compound of chemical formula (5).

COMPARATIVE EXAMPLE 4

An electrophotographic photoreceptor was prepared in the same manner as described in Example 4 except that the compound of chemical formula (2) in the electrophotographic photoreceptor of Example 4 was replaced by the compound of chemical formula (6).

EXAMPLE 7

In a paint shaker, 5 g of high-purity oxytitanium phthalocyanine was ground with 50 ml of glass beads for 100 hours, followed by wet-milling with 50 ml of n-propanol and 5 g of polyvinyl butyral for one hour and dispersion in 100 ml of a solvent methyl ethyl ketone for 10 hours. Said dispersion was dip-coated on an aluminium drum forming a conductive substrate 1 and dried to form a carrier generation layer 2 having a thickness of 0.2 μm, while a carrier transport layer 3 was formed in the same manner as described in Example 1 to prepare an electrophotographic photoreceptor.

EXAMPLE 8

An electrophotographic photoreceptor was prepared in the same manner as described in Example 7 except that the compound of chemical formula (2) in the electrophotographic photoreceptor of Example 7 was replaced by the compound of chemical formula (3).

EXAMPLE 9

An electrophotographic photoreceptor was prepared in the same manner as described in Example 7 except that the compound of chemical formula (2) in the electrophotographic photoreceptor of Example 7 was replaced by the compound of chemical formula (4).

COMPARATIVE EXAMPLE 5

An electrophotographic photoreceptor was prepared in the same manner as described in Example 7 except that the compound of chemical formula (2) in the electrophotographic photoreceptor of Example 7 was replaced by the compound of chemical formula (5).

COMPARATIVE EXAMPLE 6

An electrophotographic photoreceptor was prepared in the same manner as described in Example 7 except that the compound of chemical formula (2) in the electrophotographic photoreceptor of Example 7 was replaced by the compound of chemical formula (6).

EXAMPLE 10

In 80 parts by weight of a solvent THF were dispersed by blending 1 part by weight of the disazo pigment of formula (10) as a carrier generation material and 10 parts by weight of polycarbonate as a binder resin using a sand mill for ten hours, and 9 parts by weight of a triphenyldiamine compound of the following chemical formula (11):

(11)

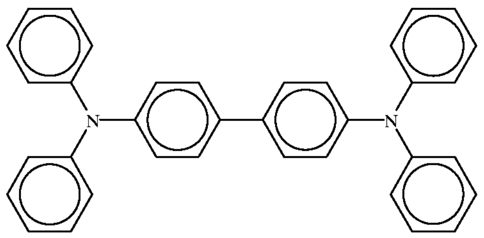

and 2 parts by weight of the compound of chemical formula (2) as carrier transport materials were further dissolved to prepare a coating fluid. Said coating fluid was dip-coated on an aluminium drum forming a conductive substrate 1 and dried at 80° C. for one hour to form a photosensitive layer 4 having a thickness of 20 $\mu$m and combining both functions of generating and transporting charge carriers, whereby an electrophotographic photoreceptor was prepared.

EXAMPLE 11

An electrophotographic photoreceptor was prepared in the same manner as described in Example 10 except that the compound of chemical formula (2) in the electrophotographic photoreceptor of Example 10 was replaced by the compound of chemical formula (3).

EXAMPLE 12

An electrophotographic photoreceptor was prepared in the same manner as described in Example 10 except that the compound of chemical formula (2) in the electrophotographic photoreceptor of Example 10 was replaced by the compound of chemical formula (4).

COMPARATIVE EXAMPLE 7

An electrophotographic photoreceptor was prepared in the same manner as described in Example 10 except that the compound of chemical formula (2) in the electrophotographic photoreceptor of Example 10 was replaced by the compound of chemical formula (5).

COMPARATIVE EXAMPLE 8

An electrophotographic photoreceptor was prepared in the same manner as described in Example 10 except that the compound of chemical formula (2) in the electrophotographic photoreceptor of Example 10 was replaced by the compound of chemical formula (6).

EXAMPLE 13

In 80 parts by weight of a solvent THF were dispersed by blending 1 part by weight of high-purity oxytitanyl phthalocyanine as a carrier generation material and 10 parts by weight of polycarbonate as a binder resin using a sand mill for ten hours, and 9 parts by weight of the triphenyldiamine compound of formula (11) and 2 parts by weight of the compound of chemical formula (2) as carrier transport materials were further dissolved to prepare a coating fluid. Said coating fluid was dip-coated on an aluminium drum forming a conductive substrate 1 and dried at 80° C. for one hour to form a photosensitive layer 4 having a thickness of 20 $\mu$m and combining both functions of generating and transporting charge carriers, whereby an electrophotographic photoreceptor was prepared.

EXAMPLE 14

An electrophotographic photoreceptor was prepared in the same manner as described in Example 13 except that the compound of chemical formula (2) in the electrophotographic photoreceptor of Example 13 was replaced by the compound of chemical formula (3).

EXAMPLE 15

An electrophotographic photoreceptor was prepared in the same manner as described in Example 13 except that the compound of chemical formula (2) in the electrophotographic photoreceptor of Example 13 was replaced by the compound of chemical formula (4).

COMPARATIVE EXAMPLE 9

An electrophotographic photoreceptor was prepared in the same manner as described in Example 13 except that the compound of chemical formula (2) in the electrophotographic photoreceptor of Example 13 was replaced by the compound of chemical formula (5).

COMPARATIVE EXAMPLE 10

An electrophotographic photoreceptor was prepared in the same manner as described in Example 13 except that the compound of chemical formula (2) in the electrophotographic photoreceptor of Example 13 was replaced by the compound of chemical formula (6).

EXAMPLE 16

After 2 parts by weight of the disazo pigment of formula (10) and 1 part by weight of polyvinyl butyral as a binder resin were dry-blended, they were dispersed in a solvent consisting of 16 parts by weight of 1,4-dioxane and 4 parts by weight of acetone for 2 hours using a sand mill, and said dispersion was dip-coated on an aluminium drum forming a conductive substrate 1 and dried to form a carrier generation layer 2 having a thickness of 0.5 $\mu$m.

Then, a coating fluid was prepared by dissolving 10 parts by weight of the triphenyldiamine compound of formula

(11) and 1 part by weight of the compound of chemical formula (2) as carrier transport materials and 10 parts by weight of polycarbonate as a binder resin in 100 parts by weight of a solvent THF, and said coating fluid was dip-coated on the drum provided with the carrier generation layer 2 and dried at 80° C. for one hour to form a carrier transport layer 3 having a thickness of 20 μm, whereby an electrophotographic photoreceptor was prepared.

EXAMPLE 17

An electrophotographic photoreceptor was prepared in the same manner as described in Example 16 except that the compound of chemical formula (2) in the electrophotographic photoreceptor of Example 16 was replaced by the compound of chemical formula (3).

EXAMPLE 18

An electrophotographic photoreceptor was prepared in the same manner as described in Example 16 except that the compound of chemical formula (2) in the electrophotographic photoreceptor of Example 16 was replaced by the compound of chemical formula (4).

COMPARATIVE EXAMPLE 11

An electrophotographic photoreceptor was prepared in the same manner as described in Example 16 except that the compound of chemical formula (2) in the electrophotographic photoreceptor of Example 16 was replaced by the compound of chemical formula (5).

COMPARATIVE EXAMPLE 12

An electrophotographic photoreceptor was prepared in the same manner as described in Example 16 except that the compound of chemical formula (2) in the electrophotographic photoreceptor of Example 16 was replaced by the compound of chemical formula (6).

Measurement Condition

Electrophotographic photoreceptors of the above Examples 1–15 and Comparative examples 1–10 were positively charged in a dark room by corona discharge with a corona discharger at a corona discharge current of 17 μA, and the initial surface potential $V_0$ and potential retentivity DDR after 10 seconds were measured. After then, each electrophotographic photoreceptor was exposed to white light to determine the exposed dose E/50 (lux×sec) at which the surface potential of each electrophotographic photoreceptor decreased by half from 700 V to 350 V. This half-decrease exposed dose is a value indicating the sensitivity of each electrophotographic photoreceptor. After the half-decrease exposed dose was determined, each electrophotographic photoreceptor was positively charged again and exposed to 20 lux for 60 seconds at a surface potential of 700 V to measure the residual potential VR.

Photoreceptors of the above Examples 16–18 and Comparative examples 11–12 were negatively charged by corona discharge at a voltage corresponding to a corona discharge current of 17 μA, and the initial surface potential $V_0$ and potential retentivity DDR after 10 seconds were measured. After then, each electrophotographic photoreceptor was exposed to white light to determine the exposed dose E/50 at which the surface potential of each electrophotographic photoreceptor decreased by half from −700 V to −350. After the half-decrease exposed dose was determined, each electrophotographic photoreceptor was negatively charged again and exposed to 20 lux for 60 seconds at a surface potential of −700 V to measure the residual potential $V_R$.

Measurement Results

The results of measurement for the above described Examples 1–18 and Comparative examples 1–12 are shown in the following Table 1.

TABLE 1

| | $V_0$ | DDR | E/50 | $V_R$ |
|---|---|---|---|---|
| Example | | | | |
| 1 | 780 | 0.79 | 11.0 | 70 |
| 2 | 770 | 0.85 | 12.0 | 50 |
| 3 | 800 | 0.90 | 5.0 | 90 |
| 4 | 750 | 0.71 | 9.0 | 30 |
| 5 | 800 | 0.78 | 9.0 | 25 |
| 6 | 780 | 0.80 | 3.0 | 50 |
| 7 | 760 | 0.80 | 9.0 | 15 |
| 8 | 780 | 0.83 | 8.0 | 20 |
| 9 | 750 | 0.81 | 3.0 | 30 |
| 10 | 720 | 0.72 | 2.3 | 30 |
| 11 | 780 | 0.80 | 2.3 | 25 |
| 12 | 750 | 0.76 | 1.8 | 20 |
| 13 | 800 | 0.72 | 1.8 | 20 |
| 14 | 770 | 0.77 | 2.0 | 30 |
| 15 | 740 | 0.70 | 1.5 | 20 |
| 16 | −770 | 0.88 | 0.9 | −20 |
| 17 | −810 | 0.93 | 0.8 | −20 |
| 18 | −780 | 0.90 | 0.7 | −15 |
| Comparative example | | | | |
| 1 | 800 | 0.92 | 15.0 | 200 |
| 2 | 750 | 0.65 | 17.0 | 150 |
| 3 | 830 | 0.90 | 12.0 | 180 |
| 4 | 720 | 0.62 | 16.0 | 150 |
| 5 | 810 | 0.86 | 12.0 | 170 |
| 6 | 730 | 0.60 | 15.0 | 120 |
| 7 | 820 | 0.87 | 2.7 | 150 |
| 8 | 700 | 0.53 | 2.5 | 110 |
| 9 | 860 | 0.85 | 2.4 | 120 |
| 10 | 710 | 0.50 | 2.7 | 100 |
| 11 | −850 | 0.95 | 1.5 | −50 |
| 12 | −750 | 0.81 | 1.4 | −40 |

Among Examples 1–9 and Comparative examples 1–6 relating to positively charged function-separated type photoreceptors wherein a carrier transport layer 3 is formed on a carrier generation layer 2 containing oxytitanium phthalocyanine or an azo pigment as a carrier generation material, Examples 1–9 having a substituent for $R^1$ was found to show better photosensitive characteristics with lower half-decrease exposed dose and much lower residual potential as compared with Comparative examples 1, 3 and 5 using chemical formula (5) which leads to molecular vibration but lacks substituent for $R^1$, as appreciated from Table 1. Said Examples 1–9 were also found to show better photosensitive characteristics than Comparative examples 2, 4 and 6 using chemical formula (6) lacking substituent for $R^1$.

Among Examples 10–15 and Comparative examples 7–10 relating to positively charged monolayer type photoreceptors wherein a carrier generation material and a carrier transport material are contained in a photosensitive layer 4, Examples 10–15 were also found to show better photosensitive characteristics than Comparative examples 7–10.

Among Examples 16–18 and Comparative examples 11–12 relating to multilayer type electrophotographic photoreceptors similar to those of Examples 1–9 but negatively charged, Examples 16–18 containing a compound of the present invention were found to show better photosensitive characteristics than Comparative examples 11–2, confirming that the compound of the present invention has sensitizing effects and lowers residual potential.

The foregoing description relates to electrophotographic photoreceptors using said organic thin films as a photosensitive layer, but the present invention is not limited thereto. For example, the present invention also includes electrophotographic photoreceptors using said organic thin films as a resin layer formed between a photosensitive layer and a conductive substrate. Organic thin films containing a compound of the above general formula (1) have a high electron mobility enough to meet a proper conductivity required for organic thin films used as a resin layer, thus provide electrophotographic photoreceptors with low residual potential. Said organic thin films can also be used as a protecting film formed on the surface of a photosensitive layer.

In brief, the present invention broadly includes electrophotographic photoreceptors comprising an organic thin film containing a compound of the above general formula (1).

As has been described, electrophotographic photoreceptors of the present invention containing an electron transfer agent in the photosensitive layer are particularly suitable for positively charged systems.

The electron transfer agent in the photosensitive layer shows high electron acceptability and strong molecular vibration enough to provide a photosensitive layer with high electron mobility, high sensitivity and low residual potential.

Moreover, the electron transfer agent has a good compatibility with binder resins so that it can be abundantly and homogeneously dispersed in the photosensitive layer without blocking incident light reaching the carrier generation material because of low tinting, thus providing an electrophotographic photoreceptor with high sensitivity.

An additional advantage of the present invention is that the molecular structure of the electron transfer agent can be designed by selecting substituents to meet desired characteristics of electrophotographic photoreceptors.

Industrial Applicability of the Invention

As apparent from the foregoing description, compounds for electrophotographic photoreceptors with good characteristics and electrophotographic photoreceptors can be obtained according to the present invention.

What is claimed is:

1. A compound of the following chemical formula (4):

(4)

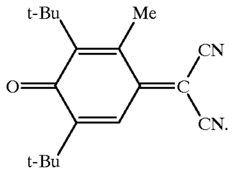

2. An electrophotographic photoreceptor comprising;

a conductive substrate, a photosensitive layer having a carrier generation material and a carrier transport material, formed on said conductive substrate, wherein said carrier transport material contains a compound of the formula (4):

(4)

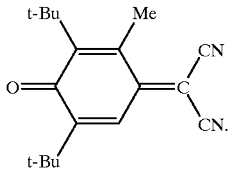

3. An electrophotographic photoreceptor comprising;

a conductive substrate, a photosensitive layer formed on said conductive substrate, wherein said photosensitive layer comprises a carrier generation layer having a carrier generation material and a carrier transport layer having a carrier transport material and wherein said carrier transport material is represented by a compound of the formula (4):

(4)

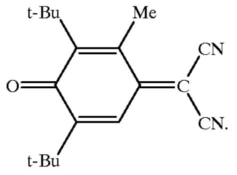

* * * * *